Figure 2:
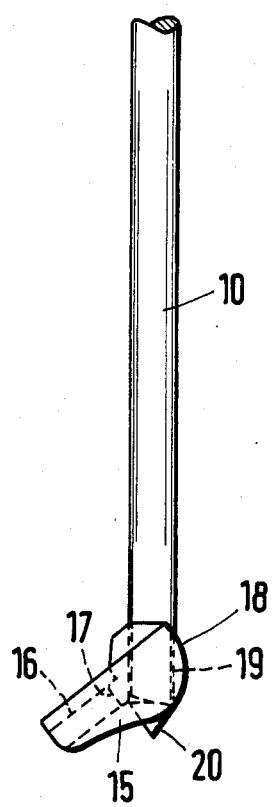

United States Patent [19]

Keller

[11] Patent Number: 4,642,121
[45] Date of Patent: Feb. 10, 1987

[54] JOINT ENDOPROSTHESIS AND INSTRUMENT FOR KNOCKING IT IN OR OUT

[75] Inventor: Arnold Keller, Kayhude, Fed. Rep. of Germany

[73] Assignee: Waldemar Link GmbH & Co, Hamburg, Fed. Rep. of Germany

[21] Appl. No.: 767,556

[22] Filed: Aug. 20, 1985

[30] Foreign Application Priority Data

Sep. 14, 1984 [DE] Fed. Rep. of Germany ....... 3433859

[51] Int. Cl.⁴ ....................... A61B 17/00; A61B 17/18
[52] U.S. Cl. ........................................ 623/18; 623/23; 128/303 R; 128/92 VT
[58] Field of Search ................ 128/303 R, 92 XT, 92, 128/92 XZ; 623/22, 23, 16, 18; 81/176.2, 176.1, 176.15

[56] References Cited

U.S. PATENT DOCUMENTS

| | | | |
|---|---|---|---|
| 922,258 | 5/1909 | Caven | 81/176.2 |
| 3,801,989 | 4/1974 | McKee | 128/92 X |
| 4,153,053 | 5/1979 | Figallo | 128/92 XT |
| 4,222,382 | 9/1980 | Antonsson et al. | 128/92 XT |

FOREIGN PATENT DOCUMENTS

| | | |
|---|---|---|
| 0027159 | 4/1981 | European Pat. Off. . |
| 2101002 | 5/1972 | Fed. Rep. of Germany . |
| 2134316 | 11/1976 | Fed. Rep. of Germany . |
| 8400642 | 7/1984 | Fed. Rep. of Germany . |
| 459462 | 9/1968 | Switzerland . |

Primary Examiner—Richard J. Apley
Assistant Examiner—H. Macey
Attorney, Agent, or Firm—Townsend and Townsend

[57] ABSTRACT

A joint endoprosthesis and an instrument for knocking it in or out, which are provided for mutual connection with collaborating ribs and grooves, on the one hand, in a fork arranged on the end of the instrument shaft and, on the other hand, on the neck of the prosthesis, the direction of the instrument shaft being transverse to the plane of the fork. To obtain a positive, play-free and sensitive connection between the instrument and the prosthesis, the end of the instrument shaft is taken as a locking pin through a threaded bore in the fork and the prosthesis contains a locking recess for receiving the locking pin.

6 Claims, 3 Drawing Figures

JOINT ENDOPROSTHESIS AND INSTRUMENT FOR KNOCKING IT IN OR OUT

DESCRIPTION

The invention relates to a joint endoprosthesis and an instrument for knocking it in or out, which are provided for mutual connection with collaborating ribs and grooves, on the one hand, in a fork arranged on the end of the instrument shaft and, on the other hand, on the neck of the prosthesis, the direction of the instrument shaft being transverse to the plane of the fork.

In known prosthesis and instrument combinations of this type, the prosthesis neck has, on each of the opposite sides, one groove in which the fork prongs of the instrument engage, the common plane of the fork prongs being inclined relative to the direction of the shaft in such a way that the knocking-in forces effect engagement of the fork with the prosthesis neck. Conversely, the knocking-out forces would pull the fork away from the prosthesis neck; the known combination is therefore unsuitable for knocking the prosthesis out. Instead, a special instrument is provided for this purpose, which grips with a hooked fork under the articular head. However, such a knocking-out instrument cannot be used in the case of prostheses with a prosthesis head which can be released via a cone joint, since in such a case the application of the instrument to the head would only effect detachment of the latter from the prosthesis stem. Moreover, the known instrument/prosthesis combination has the disadvantage that, even with precise fabrication, a certain play between the instrument fork and the grooves on the prosthesis neck cannot be excluded, so that the required very delicate rotational adjustment of the prosthesis can become more difficult.

It is the object of the invention to provide a joint endoprosthesis and an instrument, fitting it, for knocking it in or out, which do not have these disadvantages.

The object is achieved according to the invention when the end of the instrument shaft protrudes as a locking pin through a bore in the fork and the prosthesis has a locking recess for receiving the locking pin.

Advantageously, the locking recess is a bore; however, this is not absolutely necessary, because it would be possible to ensure securing of the fork on the prosthesis neck also by engagement of the locking pin in a peripheral groove. If individual recesses are provided for receiving the locking pin, namely bores, for example, several of these individual recesses are preferably distributed over the circumference or the respective circumferential arc of the prosthesis, so that the instrument can be joined to the prosthesis in differing positions, in adaptation to varying operation conditions.

According to an important feature of the invention, the locking pin and the locking recess should collaborate via at least one surface extending transversely to the direction of the shaft. This creates in fact a direct transmission of the impact force from the instrument shaft to the prosthesis—by-passing the fork—and this allows a correspondingly finer design of the fitting surfaces on the fork and on the prosthesis neck, since these surfaces have to absorb only small forces. The fork itself and its connection to the shaft can also be of correspondingly finer design, and this can be of great importance in view of the restricted space conditions in the operating field.

According to a further feature of the invention, the shaft and the bore receiving it in the fork are provided with a collaborating screw thread. On the one hand, this particularly simplifies the design of the said components, because no additional connecting elements which take up space and are prone to faults are required and, on the other hand, a simple method, which does not divert the attention of the surgeon from important problems, for actuating the connection between the instrument and the prosthesis is provided, which connection is made or released simply by rotation in one direction or the other. However, it would of course also be possible to choose a different connection technique between the shaft and the fork, which, on the one hand, allows a longitudinal movement of the shaft end, forming the locking pin, relative to the fork and, on the other hand, retains the locking pin in the locking position, for example a bayonet connection.

It can be advantageous to form the rib on the prosthesis side or the groove on the prosthesis neck as a ring. This in fact allows the operator to withdraw the fork of the instrument from the prosthesis neck in a direction other than that of the connection originally fixed by the locking, for example if the withdrawal path in the original direction of the connection is blocked or more difficult in the operating field.

The invention can be applied with particular advantage to stem prostheses, and among these in turn with particular advantage to hip joint/femur prostheses. In the case of the latter, there is in fact the possibility of letting the direction of the instrument shaft extend approximately in the direction of the prosthesis stem, and the locking bore envisaged for this position can readily be provided laterally of the prosthesis neck in the prosthesis collar or in the stem end at the latter.

Figure 1:
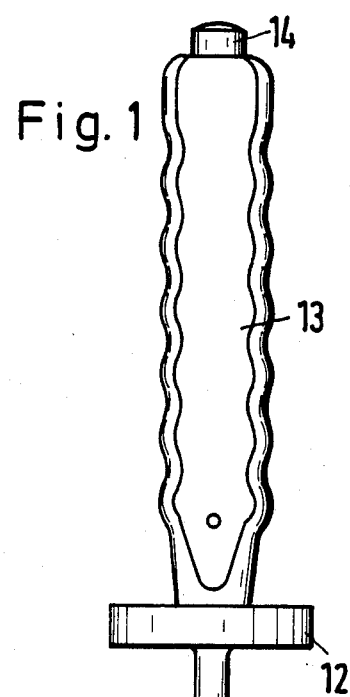
Figure 3:
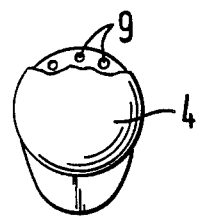

The invention is explained below in more detail by reference to the drawing which illustrates an advantageous embodiment and in which:

FIG. 1 shows an overall view of the prosthesis/instrument combination in the assembled state, on a slightly reduced scale, FIG. 2 shows a side view, corresponding to FIG. 1, of the fork end of the instrument, approximately in natural size, and FIG. 3 is a top view of a joint prosthesis with portions broken away to show several locking bores.

The prosthesis, indicated in FIG. 1 by dots and dashes, in a hip joint/femur prosthesis with stem 1, collar 2, neck 3 and articular head 4 which can be integrally joined to the neck or put in place via a cone joint. The neck forms a ring groove 7 between a ring rib 5 and a bead 6 terminating the top of the collar 2. The direction 8 of the neck 3 is angled in the known manner relative to the direction of the stem 1.

Laterally from the neck 3, the collar 2 contains a conical bore 9 as a locking bore, the position and axial direction of which approximately coincides with the centre axis of the stem 1. The lateral boundary surface of the bore 9 and the direction of the stem enclose a slightly smaller angle than the ribs and grooves 5 to 7 on the prosthesis neck.

The instrument has a shaft 10 on the end of which the fork 11 is seated. At the other end, a plate 12 is provided, the lower surface of which is provided for applying pressure by means of a hammer when the prosthesis is knocked out. This is adjoined by a handle 13, from which protrudes a projection 14 of the shaft for forming an impact surface when the prosthesis is knocked in.

The instrument can easily be manipulated by the handle 13, and torques for correcting the rotational position of the prosthesis can also be applied during implantation. If desired, the handle can also be provided transversely to the direction of the axis of the components 10, 12 and 14, if it is desired to apply larger torques.

The plane of the fork 11 is transverse to the shaft 10, namely at an angle of inclination which is complementary to the angle between the neck axis 8 and the direction of the stem 1 of the prosthesis. The dimensions are here adjusted such that the instrument shaft 10 lies approximately coaxial to the prosthesis stem 1.

The fork has two prongs 15 which are located one behind the other in the illustrations and between them form a U-shaped recess which, in the mounted state, receives the neck 3. The mutually facing surfaces of the prongs 15 here have, in symmetrical arrangement, a rib 16 (dotted and dashed in FIG. 2), the width and height of which correspond to those of the groove 7 on the neck of the prosthesis in such a way that the rib 16 engages in this groove when the instrument is connected to the prosthesis. The rib 16 can also continue as a semicircle at 17 in the bridge part connecting the prongs 15, so that maximum engagement between the ribs and grooves of the instrument and of the prosthesis can be obtained.

The bridge part 18 of the fork 11 contains a threaded bore 19 which receives the end, provided with a screw thread, of the instrument shaft 10. On the underside, the latter projects from it with the cone tip 20 as a locking pin, the cone angle of which coincides with that of the locking bore 9. This is not absolutely necessary, because it would of course also be conceivable to have a spherically made end of the locking pin collaborate with a conical locking bore. It would also be possible for both parts to be designed as close-fitting cylinders.

With the locking pin 20 retracted, the fork 11 of the instrument can be applied to the prosthesis neck from any side. By rotating the prosthesis stem, the locking pin 20 can then be lowered into the locking bore 9, play-free seating being obtained by vigorous tightening of the screw thread, and this also allows delicate manipulation of the prosthesis. At this stage, the medially collaborating surfaces of the locking bore and of the locking pin should enclose, with the longitudinal direction of the stem, a smaller angle than the ribs and grooves of the prosthesis neck and fork, so that these components are held together not only frictionally but also positively. This is specially important when the instrument is used for knocking the prosthesis out, because the forces are then transmitted only via the fork and the said lateral surface of the locking elements. This is acceptable, because the forces applied on knocking-out are in general lower than on knocking-in. By contrast, the knocking-in forces are transmitted in a straight line from the instrument shaft 10 without the detour via the fork 11 from the locking pin 20 to the locking bore 9 and hence to the prosthesis stem.

I claim:

1. In combination, a joint endoprosthesis and instrument for knocking it in or out, the instrument comprising a shaft (10) and a fork (11) having a bore (19) therein, means for securing one end of the shaft in said bore, the longitudinal axis of the shaft being transverse to the plane of the fork, the prosthesis having a neck (3), a groove and a first rib means on
   one of the neck and fork and second rib means on the other of the neck and fork for collaboration with the groove and first rib means, the one end of the shaft further comprising a locking pin (20) protruding beyond said bore when said shaft is secured in said bore and the prosthesis having a locking recess (9) for receiving the locking pin.

2. The combination of claim 1, characterised in that said groove and said first rib means (7) (5, 6) are formed as rings on the prosthesis neck (3).

3. The combination of claim 1, characterised in that the locking recess (9) is a locking bore.

4. The combination of claim 3, characterised in that the locking pin (20) and the locking bore (9) collaborate via at least one surface extending transversely to the direction of the shaft.

5. The combination of claim 1, characterised in that the shaft (10) and the bore (19) receiving it in the fork (11) are provided with collaborating screw threads as said securing means.

6. The combination of claim 1, characterised in that several locking recesses (9) are provided on the upper portion of the prosthesis.

* * * * *